United States Patent [19]

Hahn

[11] Patent Number: 5,775,911
[45] Date of Patent: Jul. 7, 1998

[54] METHOD AND APPARATUS FOR PRODUCING A SHAPED ARTICLE BY SONOEROSION

[75] Inventor: Rainer Hahn, Tübingen, Germany

[73] Assignee: Thera Patent GmbH & Co., KG Gesellschaft fuer industrielle Schutzrechte, Seefeld, Germany

[21] Appl. No.: 589,126

[22] Filed: Jan. 22, 1996

[30] Foreign Application Priority Data

Jan. 20, 1995 [DE] Germany ............ 195 01 699.8

[51] Int. Cl.⁶ .............. A61C 13/00; A61C 5/08
[52] U.S. Cl. .............. 433/223; 264/19; 451/165
[58] Field of Search .............. 433/119, 165, 433/166, 167, 173, 191, 192, 223; 264/19; 451/165

[56] References Cited

U.S. PATENT DOCUMENTS

| | | | |
|---|---|---|---|
| 2,774,193 | 12/1956 | Thatcher et al. | 433/119 |
| 3,971,133 | 7/1976 | Mushabac | 32/2 |
| 4,343,111 | 8/1982 | Inoue . | |
| 4,734,173 | 3/1988 | Walter et al. | 204/129.1 |
| 4,904,348 | 2/1990 | Domes et al. | 204/4 |
| 5,224,049 | 6/1993 | Mushabac | 433/223 |
| 5,490,810 | 2/1996 | Hahn et al. | 451/165 |
| 5,513,989 | 5/1996 | Crisio | 433/173 |
| 5,588,837 | 12/1996 | Rubeling et al. | 433/173 |

FOREIGN PATENT DOCUMENTS

| | | | |
|---|---|---|---|
| 39 28 684 | 4/1991 | Germany . | |
| 4138803 | 5/1993 | Germany | 433/223 |
| 43 42 078 | 12/1993 | Germany . | |
| 4332065 | 3/1994 | Germany | 433/223 |
| 9103211 | 3/1991 | WIPO | 433/223 |

*Primary Examiner*—Ralph Lewis
*Attorney, Agent, or Firm*—Foley & Lardner

[57] ABSTRACT

A shaped article, specifically an artificial tooth, is made of two parts. An individually shaped first part 18, specifically the head part or superstructure of the artificial tooth, has a standardized locking portion 26 for engagement with a standardized counter-locking portion 24 provided on a pre-fabricated second part 16, specifically the shaft part of the tooth to be implanted in a patient's jaw. The individually shaped part 18 is manufactured by using a pre-fabricated sonotrode 38 for producing the configuration of the locking portion 26 and one or more individually produced shaping sonotrodes 44 are used for generating the parts of the surface other than the locking portion 26. This permits the individually shaped part to be produced in an economic way yet with high precision of the locking portion.

2 Claims, 3 Drawing Sheets

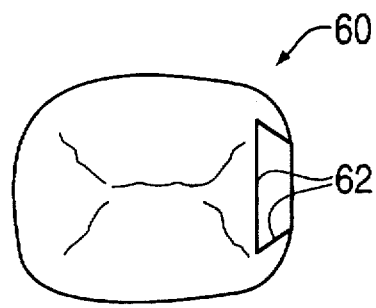
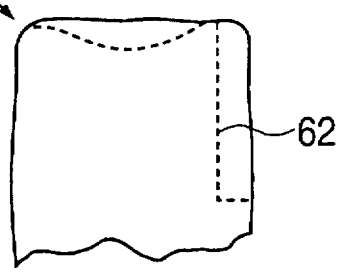
FIG. 5a   FIG. 5b
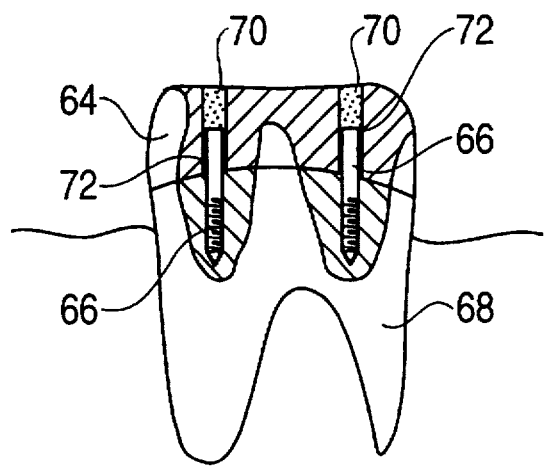
FIG. 6

METHOD AND APPARATUS FOR PRODUCING A SHAPED ARTICLE BY SONOEROSION

BACKGROUND OF THE INVENTION

The invention relates to a method and a device for manufacturing a shaped article by sonoerosion.

More specifically, the invention relates to the manufacture of a ceramic artificial tooth made of a pre-fabricated shaft part which is to be implanted in the jaw, and an individually shaped tooth superstructure to be mounted on the implanted shaft part. The superstructure has a locking portion provided in a part of its surface for engagement with a standardized counter-locking portion provided on the implanted shaft part. The locking portion of the superstructure is usually in the form of a recess, and the counter-locking portion on the shaft part is formed as a projection complementary formed with respect to the recess for snug fitting therein. By using locking and counter-locking portions of a non-circular, specifically polygonal, cross-section, accurate alignment between the axis of the shaft part and that of the superstructure and accurate mutual angular orientation about the aligned axes is achieved.

Conventionally, tooth superstructures are cast from metallic materials. It would be desirable to make them of hard ceramics. U.S. Pat. No. 3,971,133 and, similarly, published German Patent Applications 3,928,684 and 4,342,078 describe methods for making ceramic dental restoration parts by sonoerosion. The known restoration parts, however, are bridges and crowns to be mounted on tooth stumps individually prepared to receive the respective bridge or crown. There is no fitting to a pre-fabricated locking portion.

Conventional sonoerosive methods are unsuited for manufacturing such tooth superstructures as referred to above, which require a precisely fitting interlocking with a standardized shaft part. This is because sonotrodes are subject to considerable wear so that the working precision decreases with progressing penetration of the tool into the workpiece material.

SUMMARY OF THE INVENTION

It is an object of the present invention to provide a method and an apparatus for manufacturing a shaped article which has a locking portion in its surface for engagement with a standardized counter-locking portion, but is otherwise individually shaped, with a high precision fitting between the locking and counter-locking portions.

A more specific object of the invention is to manufacture an individually shaped superstructure of an artificial tooth which has a standardized locking portion for exactly fitting engagement with a standardized counter-locking portion provided on a pre-fabricated shaft part to be implanted in the jaw of a patient.

According to the present invention, a shaped article which has in part of its surface a locking portion for positive engagement with a counter-locking portion of a pre-fabricated structural part, with the remaining surface of the shaped article being individually shaped, is manufactured by using a standardized sonotrode for working the locking portion and at least one individually formed sonotrode for working the remaining surface.

The fact that a pre-fabricated sonotrode is used for producing the locking portion results in a substantially more accurate shaping of that portion than would be possible by the use of an individually formed sonotrode, such as is prepared by a dental laboratory technician prepares taking an impression of the patient's jaw and performing a number of intermediate molding steps to arrive at the final sonotrode. Each such impression and molding step is subject to certain tolerances, inaccuracies and imaging errors. While the addition of such errors may be tolerated as regards the outer shape of the tooth superstructure, it would cause unacceptable deviations in position and orientation if permitted at the locking portion.

Moreover, the active working part of a sonotrode may be made with considerably higher accuracy by automatic machine tools and high-precision measuring devices.

Also, prefabricated sonotrodes may be provided with a well-defined amount of oversizing to compensate any wear that occurs during working. Similarly, certain faces of the sonotrode may be intentionally undersized to compensate any gap caused by an abrasive used for the work.

In manufacturing a tooth superstructure having a locking portion, it has turned out proper first to work the locking section with the pre-fabricated sonotrode and subsequently work the remaining surface of the superstructure with the individually formed sonotrode. Alternatively, the two manufacturing steps may be interchanged.

While the invention is particularly useful in making artificial teeth or dental restoration parts, it is likewise applicable for a highly precise formation of slides, through-bores or the like.

BRIEF DESCRIPTION OF THE DRAWINGS

FIGS. 5(a) and 5(b) are an end view and a side view illustrating a locking structure for an artificial tooth; and FIG. 6 is a side view, partly in section, of a crowned tooth.

DETAILED DESCRIPTION OF PREFERRED EMBODIMENTS

Figure 1:
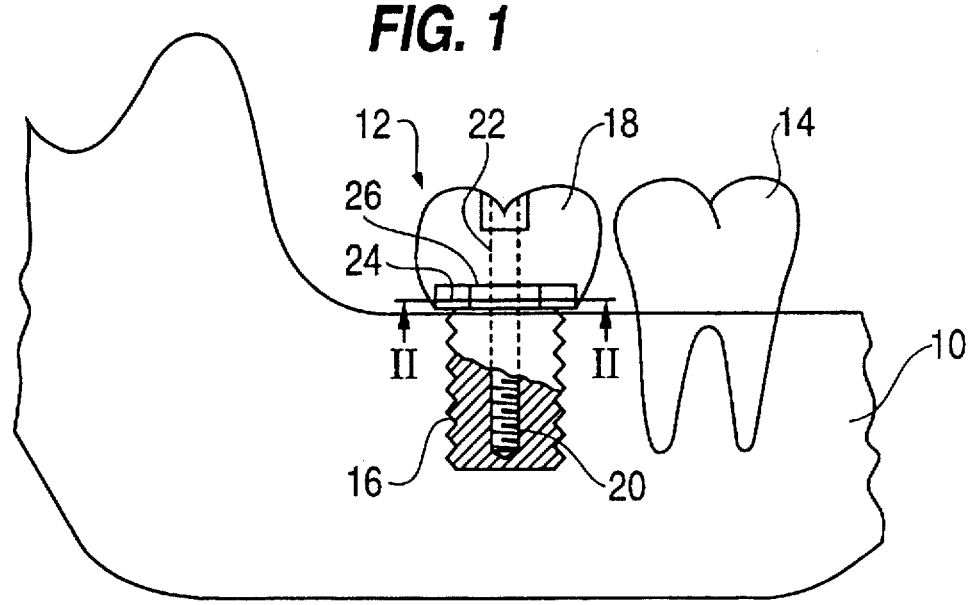
FIG. 1 is a schematic cross-sectional view of a lower jaw with an implanted artificial tooth and a natural tooth.

In the following description, the invention will be explained by reference to the field of dental restoration. The invention is not limited to this field but may be used in a variety of other technical areas FIG. 1 is a schematic partial view of a lower jaw 10 with an artificial tooth 12 next to a natural tooth 14. The artificial tooth 12 is made of an implanted shaft part 16 and a head part or superstructure 18 mounted on the shaft 16 and shaped in accordance with the upper part of the natural tooth which it replaces.

The shaft 16 is substantially cylindrical with outer cylindrical surface suitably structured to facilitate anchoring in the jaw 10. In FIG. 1, the surface structure is shown as that of a thread; other shapes and structures with recesses and projections may be used alternatively.

The shaft 16 has an axial bore 20 open to the upper surface, which extends above the jaw 10, and provided with an internal thread for receiving a fixing screw (not shown) which penetrates a through bore 22 provided in the superstructure 18. By tightening the screw, the superstructure 18 is fixed to the implanted shaft 16. The head of the fixing screw may be covered by a suitable dental cement.

With a two-part artificial tooth of this type, it is important for the superstructure 18 to be positioned and oriented with respect to the implanted shaft 16 exactly in the way designed by the dental laboratory technician. To this end, positively interlocking means are provided on the shaft 16 and superstructure 18 to prevent angular deviations in the longitudinal and circumferential directions with respect to the axis of the fixing screw.

The interlocking means include a projection 24 formed on the free end surface of the shaft 16 and a complimentarily shaped recess 26 formed in the lower surface of the superstructure 18. The peripheral surface of the projection 24 may be that of a prism with a triangular, rectangular, hexagonal, octagonal or, generally, n-angular cross section. Alternatively, it may be substantially cylindrical with a cross section that is not completely circular, for instance that of a flattened circle.

In cases where only misalignment between the axis of the through bore 22 in the superstructure 18 and the axis of the threaded bore 20 in the shaft 16 is to be prevented but rotation about these axis is permitted, a completely circular-cylindrical outer surface of the projection 24, and thus of the inner surface of the recess 26, may be used.

The following is a description of a method for manufacturing the artificial tooth 12.

After the tooth to be replaced, or the remainders thereof, has been removed and the jaw 10 exposed, the shaft 16 is implanted. Thereafter, usually after the wound has healed and the projection 24 of the shaft 16 has been exposed by surgery, an impression of the part of the jaw 10 including and surrounding the implanted shaft 16 is taken by conventional means. At this time, a dummy pin (not shown) is inserted in the threaded bore 20, which projects beyond the free surface of the implanted shaft 16. The pin extends through a sleeve (not shown) which is provided with a fitting surface for precise engagement with the projection 24.

The impression is then used to produce a positive model of gypsum or another suitable molding material which in the bottom surface of the gap to be filled by the artificial tooth has a replica of the shaft projection 24. The positive model is also provided with a cylindrical replica of the shaft 16 by filling the recess of the impression with gypsum and is positioned on the positive model of the projection 24, by means of the pin fixed in the negative model, in the same longitudinal and peripheral orientation as the shaft 16 in the jaw 10.

The technician subsequently forms, from synthetic material, a model of the superstructure, i.e. of the artificial tooth to be manufactured or of part thereof surrounding the exposed surface, particularly the projection, of the shaft model.

Upon removal and curing of the superstructure model, two sonotrodes for finishing the superstructure from two opposite sides thereof are prepared. To this end, the later working axis is defined in alignment with the axis of the pin used in taking the original impression. The positive model of the superstructure is placed on an alignment part which has the shape of the shaft projection 24 with the pin inserted in the threaded bore 20. The alignment of the working axis with the axis of the pin must be as precise as possible.

The equatorial plane of the superstructure is then determined with respect to the working axis. By conventional techniques, such as described in the above prior-art documents, the sonotrode for working the occlusal surface side of the superstructure is now prepared. Subsequently and also in accordance with conventional techniques, the counter sonotrode for working the surface of the artificial tooth from the side facing the jaw is prepared.

The manufacturing process proper for making the superstructure 18 will now be explained in more detail with reference to FIGS. 2 to 4.

Figure 2:
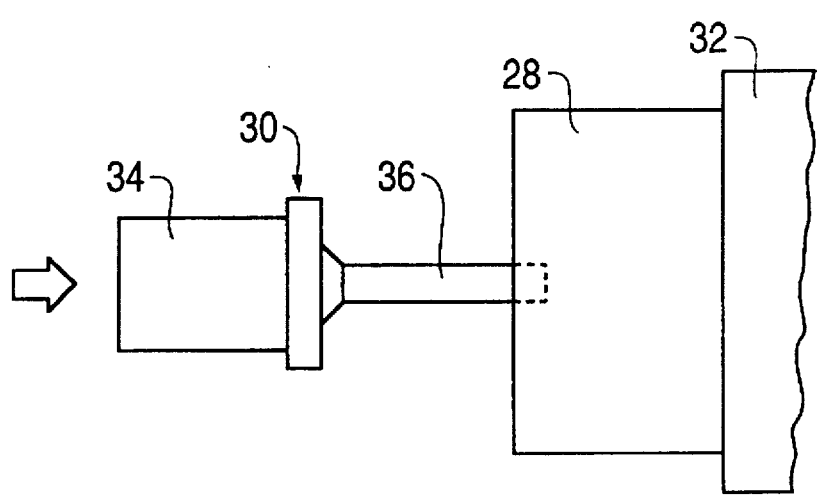
FIG. 2 illustrates part of a sonoerosion apparatus in a first step of manufacturing the artificial tooth shown in FIG. 1.

As shown in FIG. 2, a workpiece (blank) 28 of suitable size, preferably a non-worked ceramic block somewhat larger than the superstructure to be manufactured, is first worked with a pin sonotrode 30 for forming the through bore 22 (see FIG. 1) for the fixing screw that will eventually engage the threaded bore 20 of the shaft 16.

Figure 3:
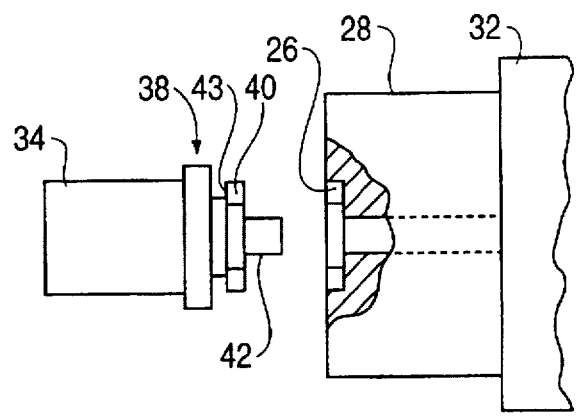
FIGS. 3 and 4 show the apparatus of FIG. 2 in second and third manufacturing steps, respectively.
Figure 4:
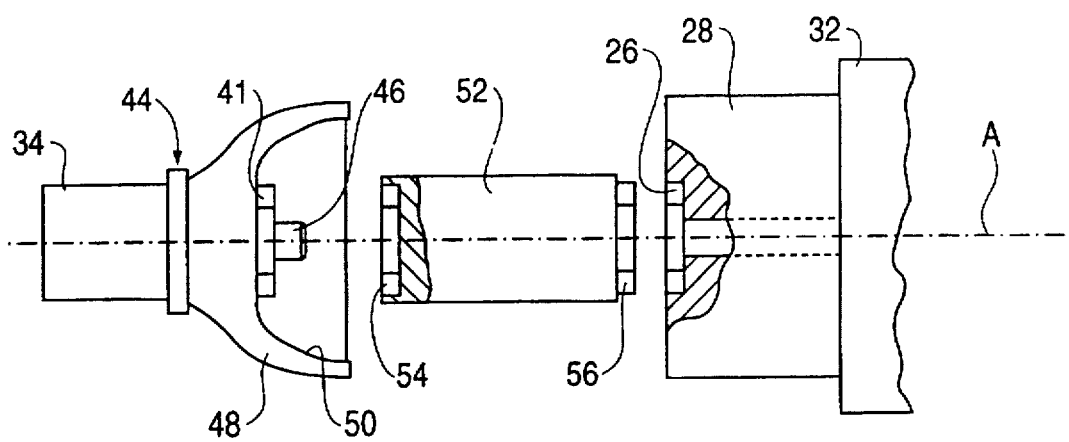

For simplifying the representation in FIGS. 2 to 4, the ultrasonic generator coupled to the respective sonotrode and associated guides and holders are not shown with the exception of part of a chuck 32 for the workpiece 28.

The pin sonotrode 30 includes a sonotrode shaft 34 to be coupled with the ultrasonic generator and a cylindrical working shaft 36 which has a diameter slightly larger than the fixing screw. The pin sonotrode 30 is advanced toward the workpiece 28 to the depth of the through bore 22 to be provided in the finished superstructure 18.

The pin sonotrode 30 is then replaced by a fitting sonotrode 38 shown in FIG. 3. The fitting sonotrode 38 is not individually made but pre-fabricated. It includes a sonotrode shaft 34 and a working portion 40 which has the same profile as the locking pojection 24 of the shaft 16. The working portion 40 carries a centering projection 42 which fits into the through bore 22 formed in the workpiece 28 to ensure the fitting sonotrode 38 to be advanced in proper alignment with the workpiece 28 in forming the locking recess 26 therein. The centering projection has proved useful in practice but is not always necessary.

During this working step, the fitting sonotrode 38, particularly the working portion 40 thereof, are subject to wear. With proper dimensioning of the working portion 40, such wear is compensated by the gap-caused by the abrasive used, so that a locking recess 26 exactly complementary to the locking projection 24 of the shaft can be formed.

Subsequently, the fitting sonotrode 38 is replaced by a shaping sonotrode 44 shown in FIG. 4 which is used to prepare the surface of the superstructure facing the jaw. This shaping sonotrode 44 includes a model 41 of the locking projection 24 of the shaft 16 and a centering projection 46 which has the same task as the centering projection 42 of the fitting sonotrode 38. The shaping sonotrode 44 has a cup-shaped wall portion 48 the inner surface 50 of which is a negative of the surface portion of the superstructure model prepared by the technician.

To ensure precise alignment and angular orientation of the shaping sonotrode 44 with respect to the workpiece 28, an adapter 52 is used, which is a cylindrical part having one end provided with a recess 54 for receiving the projection 41 formed in the shaping sonotrode 44, and its other end provided with a projection 56 for engaging the locking recess 26 formed in the workpiece 28. Upon proper alignment and orientation, the adapter 52 is removed, and the shaping sonotrode 44 is advanced toward the workpiece 28 and ultrasonically vibrated to shape the outer surface of the workpiece 28 surrounding the locking recess 26.

In working the workpiece 28 with the inner surface 50 of the shaping sonotrode 44, the projection 41 will enter the locking recess 26 previously formed in the workpiece 28. The locking recess 26 is preferably not worked by the projection 41, although some amount of working may take place depending on the precision by which the projection 41 is formed in the shaping sonotrode 44.

To take account of the working gap in this sonoerosive working, it has proved advantageous to use the same abrasive slurry for working the workpiece 28 with both the fitting sonotrode 38 and the shaping sonotrode 44.

It is possible to subdivide the step of working the workpiece 28 by means of a shaping sonotrode into two or more partial steps. Also, two identical shaping sonotrodes may be used to produce the desired shape of the workpiece by subsequent coarse and fine working. For the fine working, a new shaping sonotrode 44 is employed in the final finishing step of preparing the surface of the superstructure 18 at the side facing the jaw. Further, the fine working step may be followed by other conventional finishing steps.

Subsequently, the occlusal surface part of the workpiece 28 is worked with a counter sonotrode (not shown). To this end, the unit formed by the workpiece 28 and the shaping sonotrode 44 engaging it is separated from the ultrasonic generator and mounted on the chuck 32, while the counter sonotrode is coupled to the ultrasonic generator and aligned with respect to the first shaping sonotrode 44. The workpiece 28 is then worked at its occlusal side to prepare the final superstructure.

In another embodiment of the working method according to the invention, the locking recess 26 may first be coarse-worked by means of the individually prepared shaping sonotrode 44 and thereafter, in a second method step, finished with the pre-fabricated fitting sonotrode 38. In this embodiment, the working step illustrated in FIG. 4 would be performed prior to that shown in FIG. 3. In this case, the projection 56 provided on the adapter 52 must be dimensioned somewhat smaller than the projection 41 in the shaping sonotrode 44, which will work the locking recess 26 to its final shape.

Pre-fabricated shafts 26 are available on the market in different sizes to fit different jaws. The size of the locking projection 24 is correspondingly variable. Therefore, an according set of differently sized fitting sonotrodes 38 and adapters 54 should be available.

FIGS. 5(a) and 5(b) show a top view and a side view of a natural tooth 60 with a joining portion 62 prepared in accordance with the invention. The joining portion 62 has a dove-tail shape and serves to receive a corresponding sliding element of an artificial tooth or bridge part (not shown).

FIG. 6 shows a side view, partly in section, of a crown 64 fixed to a tooth stump 68 by means of pins 66. The connecting pins 66 are fixed in the crown 64 by means of glass solder 70 or the like. In this case, the through bores 72 in the crown 64 for the fixing pins 66 are prepared by sonoerosion in accordance with the present invention to achieve precise alignment of the bores 72.

It is claimed:

1. A method of manufacturing a shaped article which has in a part of its surface a locking portion for positive engagement with a counter-locking portion of a pre-fabricated structural part, the remaining surface of said shaped article being individually shaped, wherein said locking portion is worked with a standardized sonotrode in a first step, and a portion of said remaining surface of said shaped article surrounding said locking portion is worked with an individually formed sonotrode in a second step subsequent to said first step, said individually formed sonotrode having a fitting portion for engagement with the locking portion formed in said first step, and wherein an adapter is used for aligning said individually formed sonotrode with the locking portion formed in said first step, said adapter having a first end shaped for engagement with the locking portion of said shaped article and a second end opposite said first end shaped for engagement with the fitting portion of said individually formed sonotrode.

2. A method of manufacturing a superstructure of an artificial tooth which has in a part of its surface a locking portion for positive engagement with a counter-locking portion of a pre-fabricated shaft part of the tooth to be implanted in a jaw, the remaining surface of said superstructure being individually shaped, the method comprising the steps of:

(a) implanting said shaft part into the jaw, (b) taking an impression of the portion of the jaw including and surrounding the implanted shaft part, (c) forming a positive model of the superstructure of the artificial tooth to be produced, (d) preparing first and second individually formed sonotrodes from opposite sides of said positive model, (e) preparing a ceramic blank and forming a bore therein by using a pin-shaped sonotrode, (f) forming said locking portion in said ceramic blank by using a standardized sonotrode, said standardized sonotrode having a centering pin engaging the bore formed in step (e), (g) aligning said first sonotrode formed in step (d) with the locking portion formed in said ceramic blank and working part of said remaining surface of the blank surrounding said locking portion with said first sonotrode, and (h) working the opposite side of said blank with said second sonotrode formed in step (d).

* * * * *